United States Patent
Sherwood

(10) Patent No.: US 7,120,008 B2
(45) Date of Patent: Oct. 10, 2006

(54) METHOD AND APPARATUS FOR CAPACITOR INTERCONNECTION USING A METAL SPRAY

(75) Inventor: Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/124,983

(22) Filed: May 9, 2005

(65) Prior Publication Data

US 2006/0023396 A1 Feb. 2, 2006

Related U.S. Application Data

(60) Provisional application No. 60/588,905, filed on Jul. 16, 2004.

(51) Int. Cl.
*H01G 4/30* (2006.01)

(52) U.S. Cl. .................. 361/301.4; 361/329; 361/508; 361/516; 29/25.03

(58) Field of Classification Search ........ 361/508–509, 361/516, 528–529, 531–532, 301.4, 329, 361/303, 523–525; 29/25.03, 25.41, 25.42; 607/5, 9
See application file for complete search history.

(56) References Cited

U.S. PATENT DOCUMENTS

| | | | |
|---|---|---|---|
| 3,818,177 A | 6/1974 | Needham et al. | |
| 3,894,210 A | 7/1975 | Smith et al. | |
| 3,993,508 A | 11/1976 | Erlichman | |
| 4,033,848 A | 7/1977 | Strempel et al. | |
| 4,059,216 A | 11/1977 | Meyer | |
| 4,086,148 A | 4/1978 | Badia | |
| 4,107,022 A | 8/1978 | Strempel et al. | |
| 4,169,003 A | 9/1979 | Dangel et al. | |
| 4,171,477 A | 10/1979 | Funari | |
| 4,384,188 A | 5/1983 | Wright, Jr. | |
| 4,562,511 A | 12/1985 | Nishino et al. | |
| 5,144,523 A * | 9/1992 | Pageaud et al. | 361/308.1 |
| 5,302,414 A | 4/1994 | Alkhimov et al. | |
| 5,660,737 A | 8/1997 | Elias et al. | |
| 5,777,428 A * | 7/1998 | Farahmandi et al. | 313/352 |
| 5,968,210 A | 10/1999 | Strange et al. | |
| 6,094,339 A * | 7/2000 | Evans | 361/516 |
| 6,094,788 A | 8/2000 | Farahmandi et al. | |
| 6,162,264 A | 12/2000 | Miyazaki et al. | |
| 6,204,476 B1 | 3/2001 | Reynolds et al. | |
| 6,275,372 B1 | 8/2001 | Vassallo et al. | |
| 6,442,015 B1 * | 8/2002 | Niiori et al. | 361/502 |

(Continued)

FOREIGN PATENT DOCUMENTS

GB 825900 12/1959

(Continued)

*Primary Examiner*—Nguyen T. Ha
(74) *Attorney, Agent, or Firm*—Schwegman, Lundberg, Woessner, & Kluth, P.A.

(57) ABSTRACT

The present subject matter includes a capacitor stack having a first element having at least one first anode and at least one first cathode and a second element having at least one second anode and at least one second cathode. The capacitor stack is formed by the process of aligning the first element and the second element so that a first anode edge face of the first anode and a second anode edge face of the second anode form an anode connection surface for electrical connection of the first anode and the second anode. Additionally, the capacitor stack is formed by spraying metal on the anode connection surface to electrically connect the first anode and the second anode.

27 Claims, 9 Drawing Sheets

U.S. PATENT DOCUMENTS

| | | | |
|---|---|---|---|
| 6,556,863 B1 | 4/2003 | O'Phelan et al. | |
| 6,558,437 B1 * | 5/2003 | Wei et al. | 29/25.03 |
| 6,560,089 B1 * | 5/2003 | Miltich et al. | 361/509 |
| 6,585,152 B1 | 7/2003 | Farahmandi et al. | |
| 6,631,072 B1 | 10/2003 | Paul et al. | |
| 6,687,118 B1 | 2/2004 | O'Phelan et al. | |
| 6,699,265 B1 | 3/2004 | O'Phelan et al. | |
| 6,709,946 B1 | 3/2004 | O'Phelan et al. | |
| 6,763,265 B1 | 7/2004 | O'Phelan et al. | |
| 6,833,987 B1 * | 12/2004 | O'Phelan | 361/508 |
| 6,885,887 B1 | 4/2005 | O'Phelan et al. | |
| 7,013,561 B1 * | 3/2006 | Nakatani et al. | 29/852 |
| 2001/0020319 A1 | 9/2001 | Farahmandi et al. | |
| 2003/0030969 A1 | 2/2003 | Farahmandi et al. | |
| 2003/0195568 A1 | 10/2003 | O'Phelan et al. | |
| 2004/0019268 A1 | 1/2004 | Schmidt et al. | |
| 2004/0032698 A1 | 2/2004 | Paul et al. | |
| 2004/0114311 A1 | 6/2004 | O'Phelan et al. | |
| 2004/0127952 A1 | 7/2004 | O'Phelan et al. | |
| 2004/0147960 A1 | 7/2004 | O'Phelan et al. | |
| 2004/0147961 A1 | 7/2004 | O'Phelan et al. | |
| 2004/0173835 A1 | 9/2004 | Schmidt et al. | |
| 2004/0174658 A1 | 9/2004 | O'Phelan et al. | |
| 2004/0193221 A1 | 9/2004 | O'Phelan et al. | |
| 2004/0215281 A1 | 10/2004 | O'Phelan et al. | |
| 2004/0220627 A1 | 11/2004 | Crespi et al. | |
| 2005/0017888 A1 | 1/2005 | Sherwood et al. | |

FOREIGN PATENT DOCUMENTS

| | | |
|---|---|---|
| WO | WO-98/54739 A1 | 12/1998 |
| WO | WO-00/19470 A1 | 4/2000 |
| WO | WO-02/37515 A2 | 5/2002 |

* cited by examiner

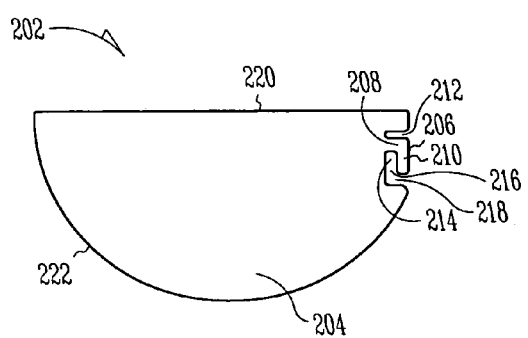
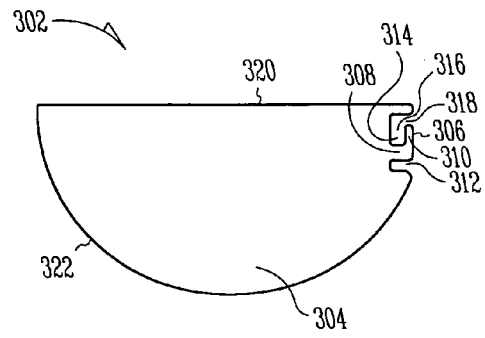
FIG. 2A          FIG. 2B
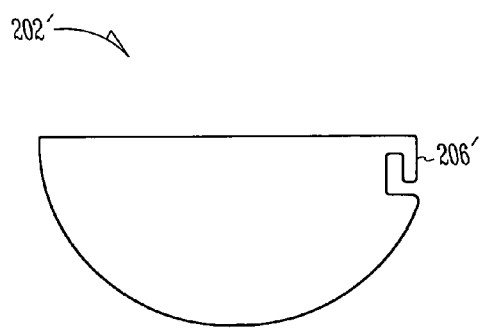
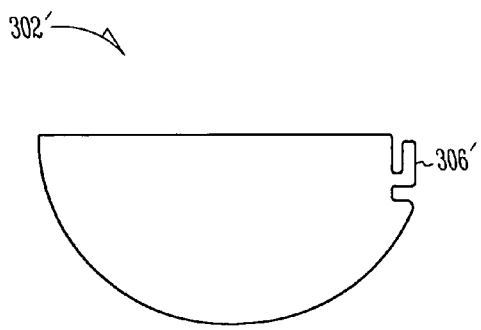
FIG. 3A          FIG. 3B

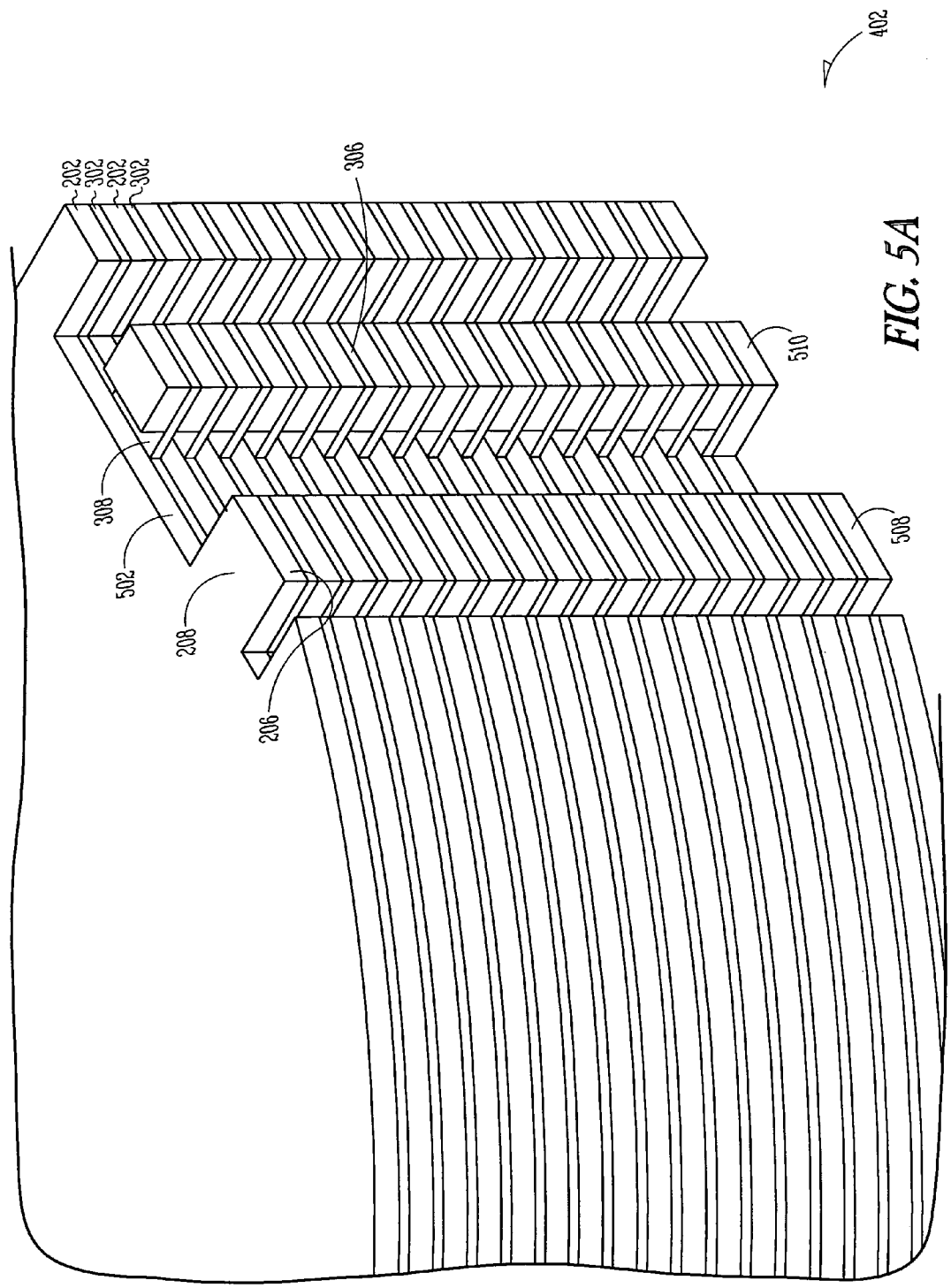

METHOD AND APPARATUS FOR CAPACITOR INTERCONNECTION USING A METAL SPRAY

CROSS REFERENCE TO RELATED APPLICATIONS

The present application is related to the following commonly assigned U.S. patents which are incorporated by reference in their entirety: "High-Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004. Additionally, the present subject matter is related to the following Provisional U.S. Patent Application which is assigned to the same assignee and is incorporated by reference in its entirety: "Method and Apparatus for Single High Voltage Aluminum Capacitor Design," Ser. No. 60/588,905, filed on Jul. 16, 2004. Further, the present application is related to the following commonly assigned copending U.S. patent application which is incorporated by reference in its entirety: "Method and Apparatus for Interconnecting Cathodes with Partial Titanium Coating," Ser. No. 11/124,706, filed on May 9, 2005.

TECHNICAL FIELD

This disclosure relates generally to capacitors, and more particularly, to a method and apparatus for capacitor interconnection using a metal spray.

BACKGROUND

There is an ever-increasing interest in making electronic devices physically smaller. Consequently, electrical components become more compact as technologies are improved. However, such advances in technology also bring about additional problems. One such problem involves interconnects between various components and interconnects within components.

Interconnects are especially problematic with devices incorporating multiple layers. One such component is the capacitor. Capacitors provide improved charge storage and energy density using multiple conductive layers and advanced dielectrics. As the layers become more complex and smaller in dimensions, problems arise with interconnections.

Thus, there is a need in the art for improved technologies for interconnects between layered devices. The systems used to interconnect the multiple layers should be readily adapted for manufacturing. The interconnects should form robust connections without damaging the multiple layers and without sacrificing substantial performance of the component.

SUMMARY

The above-mentioned problems and others not expressly discussed herein are addressed by the present subject matter and will be understood by reading and studying this specification.

One embodiment of the present subject matter includes a capacitor stack, including a first element having at least one first anode and at least one first cathode and a second element having at least one second anode and at least one second cathode, wherein the capacitor stack is formed by the process of aligning the first element and the second element so that a first anode edge face of the first anode and a second anode edge face of the second anode form an anode connection surface for electrical connection of the first anode and the second anode and spraying metal on the anode connection surface to electrically connect the first anode and the second anode.

An additional embodiment includes forming a first element by stacking a first anode and a first cathode, the first element having a first anode edge face; forming a second element by stacking the second anode and the second cathode, the second element having a second anode edge face for electrical connection to the first anode edge face; stacking the first element and the second element; aligning the first anode edge face with the second anode edge face, the alignment defining an anode connection surface; and spraying metal onto the anode connection surface to form a weld, the weld connecting the first anode and the second anode and forming a capacitor stack.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIG. 2A is a top view of an anode foil for use in constructing a capacitor according to one embodiment of the present invention;

FIG. 2B is a top view of a cathode foil for use in constructing a capacitor according to one embodiment of the present invention;

FIG. 3A is a top view of an anode foil for use in constructing a capacitor according to one embodiment of the present invention;

FIG. 3B is a top view of a cathode foil for use in constructing a capacitor according to one embodiment of the present invention;

FIG. 5A is a perspective view of the stack of FIG. 4 after the stack has been processed according to one embodiment of the present invention;

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references may contemplate more than one embodiment. The following detailed description is, therefore, not to be taken in a limiting sense, and the scope is defined only by the appended claims, along with the full scope of legal equivalents to which such claims are entitled.

Figure 1:
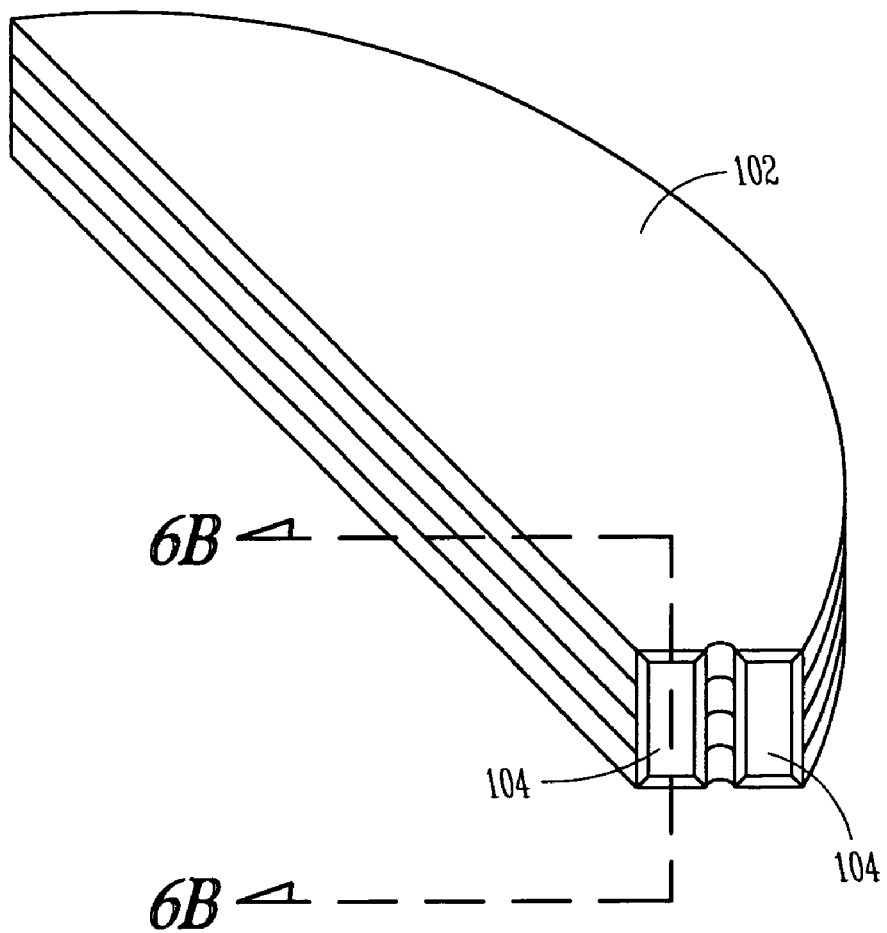
FIG. 1 is a perspective view of a capacitor stack 102, according to one embodiment of the present subject matter.

FIG. 1 is a perspective view of a capacitor stack 102, according to one embodiment of the present subject matter. Various examples of capacitor stack 102 include alternating anode and cathode layers separated by separator paper. Various embodiments include from 16 substantially planar cathode layers to 20 substantially planar cathode layers, and from 52 substantially planar anode layers to 64 substantially planar anode layers. One embodiment includes approximately 18 substantially planar cathode layers, and approximately 58 substantially planar anode layers. Various embodiments include anode layers positioned adjacent to one another without a separator.

In various embodiments, the anode of the capacitor stack 102 includes multiple interconnected anode layers. Additionally, in various embodiments, the cathode of capacitor stack 102 includes multiple interconnected cathode layers. In various embodiments, interconnection 104 connects multiple electrode layers. Some examples of interconnection 104 comprise a metallic weld. Of these, various processes include deposition of the metallic weld onto the capacitor stack 102 through spraying metal. Spraying metal, in various embodiments, is a process including both atomizing metal with a heat source and blowing metal onto the capacitor stack 102 with a directed gas flow. As will be further discussed herein, a variety of heating methods are within the scope of the present subject matter.

In various embodiments, each anode layer is approximately 0.004 inches thick. Additionally, in various embodiments, each cathode layer is approximately 0.001 inches thick. In various embodiments, a separator ranges from approximately 0.00045 and 0.00055 inches thick, and in various embodiments, the anodes are isolated from the cathodes by two sheets of approximately 0.0005 inch thick separator paper.

One method of adjusting the thickness of an electrode stack 102 is by adding or subtracting one or more electrode or separator layers. Varying the numbers of anodes and cathodes changes the electrode stack thickness. Additionally, varying the numbers of anodes and cathodes can balance the electric field strength of the anode and the electrode field strength of the cathode. These embodiments result in capacitor stacks of various sizes and shapes. For example, in one embodiment, a capacitor stack has a mass of between approximately 10.2 grams and 11.1 grams.

Various embodiments include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

The energy storing capacity of the present subject matter is due, in part, to anode foils which include an aluminum substrate at least partially encased in a dielectric. Various dielectrics include metallic oxide layers such as aluminum oxide ($Al_2O_3$). In various embodiments, dielectric layers have a thickness sufficient to withstand approximately 441 volts or greater. In one embodiment, layers have a thickness sufficient to withstand up to 600 volts. Other embodiments withstand from about 600 volts to about 800 volts or greater.

In various embodiments, the anode layers have a dielectric thickness sufficient to withstand approximately 455 volts to approximately 575 volts during operation. In some embodiments, anode layers have a dielectric thickness sufficient to withstand between about 490 volts and about 540 volts during operation. Other embodiments withstand from about 500 volts to about 530 volts during operation. One embodiment is able to withstand about 515 volts during operation.

In various embodiments, dielectric layers on anodes have a thickness conforming to and covering the etched surface to a height of from about 455 nanometers to about 575 nanometers. Additional embodiments include dielectric layers ranging from about 573 nm to about 1200 nm. In some embodiments, dielectric layer ranges from about 490 nanometers to about 540 nanometers. Other embodiments range from between about 500 nanometers to about 530 nanometers. One embodiment includes a dielectric layer thickness of approximately 515 nm. An additional embodiment has a thickness conforming to and covering the substrate to a height of at least 540 nm. It should be noted that due to the nature of the formation of a dielectric surface variations in thicknesses can occur.

FIG. 2A shows an anode 202 according to one embodiment of the present invention. Anode 202 is shown before it is assembled into capacitor stack 102 as shown in FIG. 1. Anode 202 includes a main body portion 204 having one or more connection members 206. In one embodiment, connection member 206 includes one or more separate members attached to the anode by welding, staking, or other connection method.

In various embodiments, connection member 206 is an integral portion of anode 202, and is punched, laser-cut, or otherwise shaped from the anode. In one such embodiment, portions of connection member 206 are not etched along with the rest of anode 202. For instance, a resin mask is put on portions of connection member 206 to keep those masked portions from becoming etched during the etching process. As is discussed herein, this provides for unetched, non-porous sections which improve the weldability of anode edges with respect to each other. In various embodiments, applying a mask to an anode layer includes, in part, application of a mask as is discussed in related Provisional U.S. Patent Application "Method and Apparatus for Single High Voltage Aluminum Capacitor Design," Ser. No. 60/588,905, filed on Jul. 16, 2004 on or around pages 32–34 of U.S. patent app. Ser. No. 60/588,905, the teachings of which are incorporated herein by reference, but not by way of limitation.

Connection member 206 includes a proximal section 208 and distal section 210. In the embodiment of FIG. 2A, connection member 206 is an L-shaped member. However, it can also have other shapes, including a tab shape extending away from the electrode without changing direction. In one embodiment, a portion of distal section 210 is unetched along its outer edge. Embodiments without etching arise from punching operations, as discussed above, or from other operations.

In one embodiment, proximal section 208 is connected to main body 204 and is defined in part by a pair of cut-out portions 212 and 214 located on opposing sides of proximal section 208. Distal section 210 is connected to a portion of proximal section 208. In one embodiment, it is integral with proximal section 208. In some embodiments, distal section 210 is attached as a separate member. In one embodiment, distal section 210 is defined in part by a cut-out portion 216 which is located between main body 204 and distal section 210, and a cut-out portion 218 which separates distal section 210 from main body 204.

In this embodiment, connection member 206 is located within the general perimeter or outline of anode 202. In other embodiments, connection member extends further from the main body of anode 202 or connection member 206, or is more internal within the main body of anode 202.

In some embodiments, each anode foil in capacitor stack 102 includes a connection member such as connection member 206. In other embodiments, one or more anode foils in a multi-anode stack have a connection member 206 while the other anode foils in the multi-anode stack are connected to the anode having the connection member. For instance, in one embodiment, a three-foil anode stack includes one foil having a connection member 206 and two foils without connection members. The two foils without connection members are welded, staked, or otherwise attached to the foil having the connection member.

FIG. 2B shows a cathode 302 according to one embodiment of the present subject matter. Cathode 302 is shown before it is assembled into capacitor stack, such as the capacitor stack 102 shown in FIG. 1. Cathode 302 includes a main body portion 304 having one or more connection members 306. In one embodiment, connection member 306 is an integral portion of cathode 302, and is punched, laser-cut, or otherwise shaped from the cathode. In one embodiment, connection member 306 includes one or more separate members attached to the cathode by welding, staking, or another connection method. Related Provisional U.S. Patent Application "Method and Apparatus for Single High Voltage Aluminum Capacitor Design," Ser. No. 60/588,905, filed on Jul. 16, 2004 discusses additional joining methods on or around pages 13–29 which are incorporated here by reference not by way of limitation.

In various embodiments, portions of connection member 306 are not coated in, for example, a titanium coating. For instance, in one embodiment, a titanium etchant is applied to portions of connection member 306 to substantially remove titanium coating from those portions. In some embodiments, the cathode connection member 306 is first welded to one or more anode connection members 206, and is then cut away from the respective main cathodic body 304. As such, in use there are portions of the cut-away cathode connected to an anode. Various embodiments remove a coating as is discussed in related application "Method and Apparatus for Interconnection Cathodes with Partial Titanium Coating," Ser. No. 11/124,706 at or around pages 8–25, incorporated herein by reference not by way of limitation.

Welding performed to anodes can damage dielectric boundaries, requiring post-welding aging, in various embodiments. In cases where portions of at least one cutaway cathode are attached to the anode, it is beneficial to avoid weld compositions including titanium. Titanium is derived from a cut-away cathode, in various examples. Titanium in the weld can reduce the effectiveness of oxide growth during aging. By limiting the amount of titanium in the weld, the effectiveness of aging is improved, which can result in improved capacitor performance in various embodiments. Thus, cut-away cathodes with titanium substantially absent from welding areas benefit capacitor performance during aging and overall.

In one embodiment, connection member 306 includes a proximal section 308 and a distal section 310. In the embodiment of FIG. 2B, connection member 306 is an L-shaped member. However, in additional embodiments it is shaped otherwise.

In one embodiment, proximal section 308 is connected to main body 304 and is defined in part by a pair of cut-out portions 312 and 314 located on opposing sides of proximal section 308. Distal section 310 is connected to a portion of proximal section 308. In one embodiment, it is integral with proximal section 308. In some embodiments, distal section 310 is attached as a separate member. In one embodiment, distal section 310 is defined in part by a cut-out portion 316 which is located between main body 304 and distal section 310, and a cut-out portion 318 which separates distal section 310 from main body 304.

In this embodiment, connection member 306 is located within the general perimeter or outline of cathode 302. In other embodiments, connection member 306 extends further from the main body of cathode 302 or connection member 306 is more internal within the main body of cathode 302.

FIGS. 3A and 3B show an anode 202' and a cathode 302' according to one embodiment of the present invention. Anode 202' and cathode 302' are shown before being assembled into capacitor stack 102 as shown in FIG. 1. Anode 202' and cathode 302' are generally similar to anode 202 and cathode 302, respectively, except connection member 206' does not include a cut-out such as cut-out 212 of anode 202 and connection member 306' does not include a cut-out such as cut-out 318 of cathode 302. Other embodiments utilize other shapes and locations for connection members such as connection members 206, 206', 306, and 306'.

For instance, in various embodiments, connection members 206 and 306 may be in different positions along the edges or even within the main body portions of the capacitor foils 202 and 302. For instance, in some embodiments connection members 206 and 306 are located along edges 220 and 320 of the respective foils 202 and 302. In some embodiments, the portions are located along curved edges 222 and 322 of the respective foils 202 and 302. In other embodiments, the portions may be cut-out within main bodies 204 and 304.

In one embodiment, proximal section 308 of cathode 302 and proximal section 208 of anode 202 are located in different positions (relative to each other) on their respective foils, while distal sections 210 and 310 are generally commonly positioned. For instance, in one embodiment connection members 206 and 306 of the anode 202 and the cathode 302, respectively, are mirror images of each other. In some embodiments, connection members 206 and 306 have generally reverse images of each other. In some embodiments, connection members 206 and 306 can have different shapes or sizes relative to each other. For example, the distal portions on either the anode or the cathode can be longer or shorter than its opposing distal portion.

Figure 4:
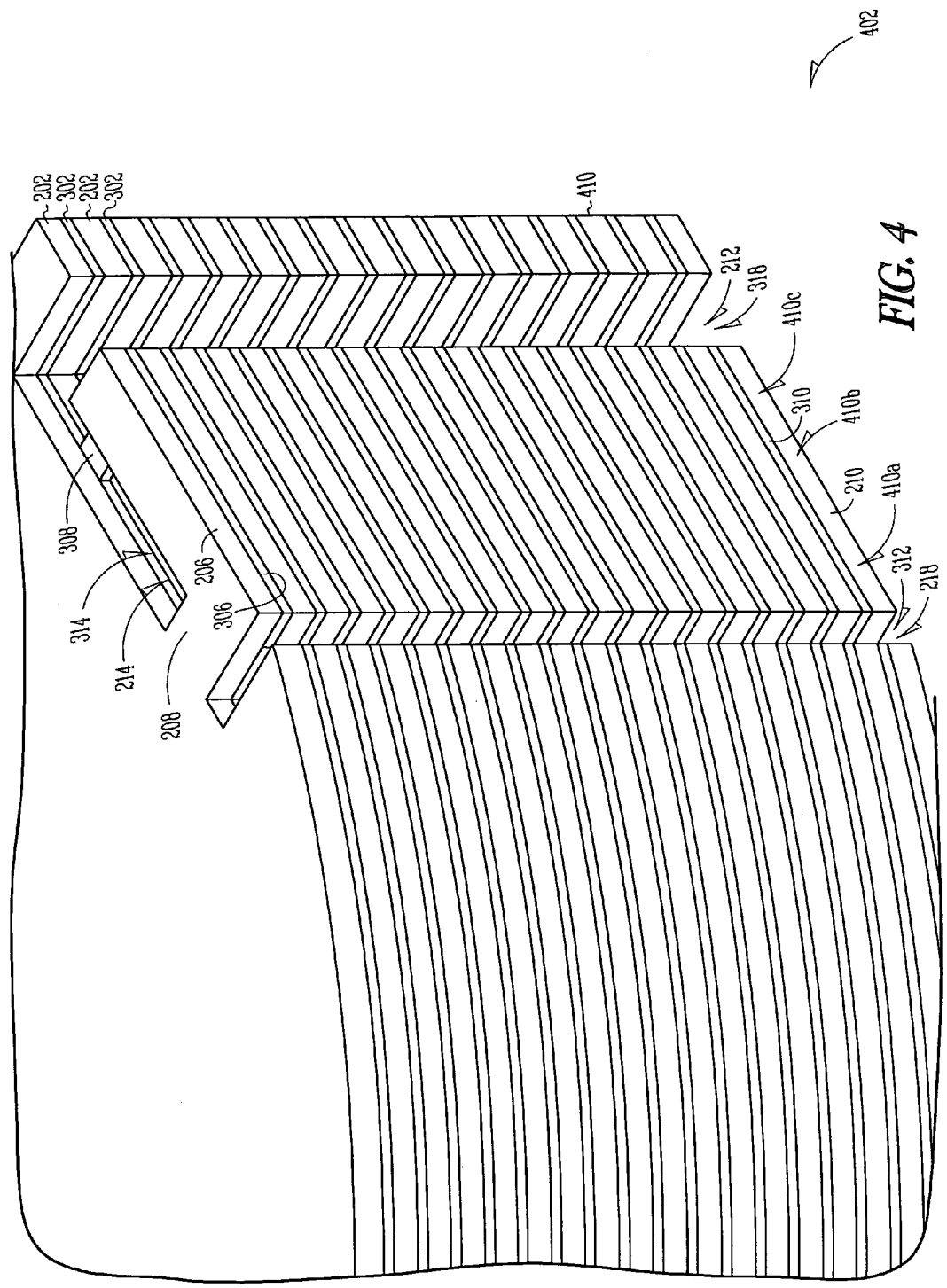
FIG. 4 is a perspective view of a stack of one or more anodes and cathodes of FIGS. 2A and 2B.

FIG. 4 shows a stack 402 of one or more alternating anodes 202 and cathodes 302. As shown in FIG. 4, connection members 206 and 306 are overlaying and underlying each other. As used herein, overlay and underlay refer to the position or location of portions of the foils which are commonly positioned from a top view. In the embodiment of FIG. 4, it is seen that connection members 206 and 306 have some commonly positioned portions relative to each other and some portions which are exclusively positioned relative to each other.

For instance, proximal sections 208 of anodes 202 are exclusively positioned or located. This means that at least a portion of proximal sections 208 do not overlay or underlay a portion of cathodes 203. Likewise, proximal sections 308 of cathodes 302 are exclusive portions and include at least a portion not overlaying or underlaying a portion of anode 202. Conversely, distal sections 210 and 310 are commonly positioned and each include at least a portion overlaying or underlaying each another. Cut-out portions 214 and 314 are also commonly positioned. Cut-out 218 is commonly positioned with cut-out 312 while cut-out 212 is commonly positioned with cut-out 318.

When stacked as shown in FIG. 4, the edges of distal sections 210 and 310 form a surface 410. In this embodiment, surface 410 can generally be described as having a first portion 410a which fronts the proximal sections 208 of anodes 202, a second portion 410b which fronts common cut-portions 214 and 314, and third portion 410c which fronts the proximal sections 308 of cathodes 302.

In this embodiment, distal sections 210 and 310 of anode connection member 206 and cathode connection member 306 are fully overlaying one another. Fully overlaying means that there are generally no gaps along surface 410 of stack 402 when the anodes and cathodes are stacked as in FIG. 4. The fully overlaid structure of stack 402 provides a complete surface 410 which provides for ease of edge-welding or otherwise connecting connection members 206 and 306 together, as will be described below. Additional embodiments, including those discussed herein, leave one or more gaps in surface 410 when the anodes and cathodes are stacked. For instance, in some embodiments, one or more of distal sections 210 or 310 may not reach all the way across front surface 410.

After being stacked, at least portions of connection members 206 and 306 are connected to each other, in various embodiments. For instance, in one embodiment portions of distal sections 210 and 310 are connected to each other. In one embodiment, distal sections 210 and 310 are edge-welded all along surface 410. In one embodiment, distal sections 210 and 310 are only connected along portion 410a and 410c of surface 410. In one embodiment, distal sections 210 and 310 are soldered along surface 410. In some embodiments, portions of distal sections 310 and 210 are staked, swaged, laser-welded, or connected by an electrically conductive adhesive. In other embodiments, portions of proximal sections 208 are connected to each other and/or portions of proximal sections 308 are connected to each other.

After being connected, portions of connection members 206 and 306 are removed or separated so that proximal sections 208 and 308 are electrically isolated from each other. As used herein, electrically isolated means that sections 208 and 308 are electrically insulated from each other at least up to a surge voltage of capacitor 100.

FIG. 5A shows stack 402 after portions of distal sections 210 and 310 have been removed from the stack, forming a separation 502 between anode connection members 206, which together comprise anode connection section 508, and cathode connection members 306, which together comprise cathode connection section 510. Separation 502 in the present embodiment electrically isolates section 508 from section 510. Proximal sections 308 are still electrically coupled to each other as are proximal sections 208. In some embodiments, separation 502 is a thin slice. In some embodiments, separation 502 is as wide as cut-outs 214 and 314, as shown in FIG. 4. In some embodiments, an electrically insulative material is inserted in separation 502. In various embodiments, separation 502 is formed by laser cutting, punching, and/or tool or machine cutting.

Figure 5B:
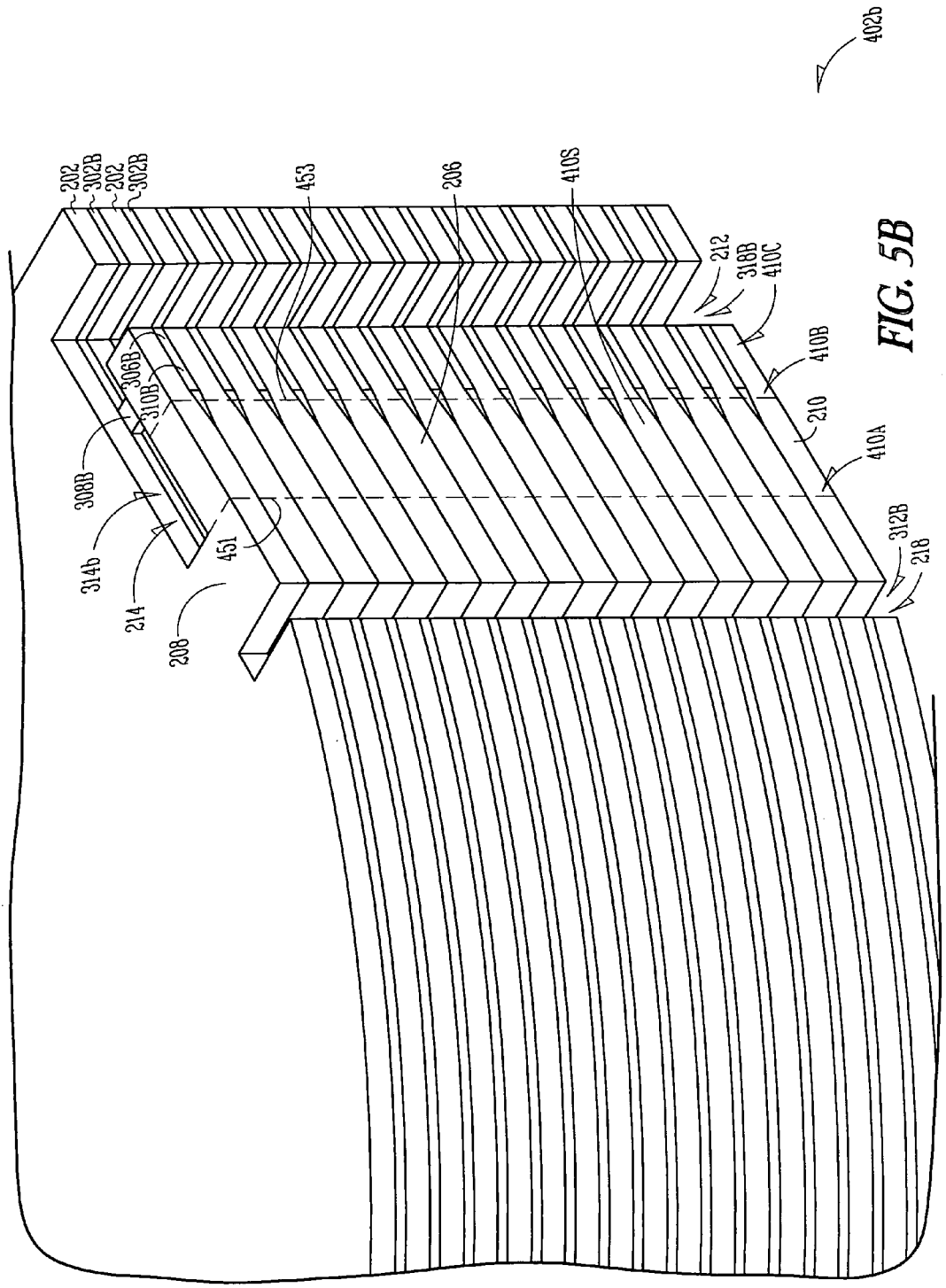
FIG. 5B is a perspective view of a stack of anodes and cathodes according to one embodiment.

FIG. 5B shows a stack 402B of one or more alternating anodes 202 and cathodes 302B, in accordance with one embodiment. Anodes 202 are as discussed above. In this example, cathodes 302B can include the features discussed above for other cathodes and the above discussion is incorporated herein. Cathodes 302B have a shorter distal section 310B than the example discussed above in FIG. 4, for example. Distal section 310B can be L-shaped as discussed above or the connection member can be straight out from the cathode body forming an I-shape. As shown in FIG. 5B, connection members 206 and 306B include at least a portion that is overlaying and underlying each other. As noted above, overlay and underlay refer to the position or location of portions of the foils which are commonly positioned from a top view. In the embodiment of FIG. 5B, it is seen that connection members 206 and 306B have some commonly positioned portions relative to each other and some portions which are exclusively positioned relative to each other.

For instance, proximal sections 208 of anodes 202 are exclusively positioned or located. This means that at least a portion of proximal sections 208 do not overlay or underlay a portion of cathodes 302B. Likewise, in one embodiment, proximal sections 308B of cathodes 302B are exclusive portions and include at least a portion not overlaying or underlaying a portion of anode 202. Moreover, in this example, distal portion 310B of cathodes 302B does not extend across the entire distal portion 210 of the anodes 202. Distal sections 210 and 310B do include a commonly positioned portion along portion 410c where each includes at least a portion overlaying or underlaying each another. Cut-out portions 214 and 314B are also commonly positioned. Cut-out 218 is commonly positioned with cut-out 312B while cut-out 212 is commonly positioned with cut-out 318B.

When stacked as shown in FIG. 5B, the edges of distal sections 210 and 310B form a surface 410S. In this embodiment, surface 410S can generally be described as having a first portion 410a which fronts the proximal sections 208 of anodes 202, a second portion 410b which fronts common cut-portions 214 and 314B, and third portion 410c which fronts the proximal sections 308B of cathodes 302B.

In this embodiment, distal sections 210 and 310B of anode connection member 206 and cathode connection member 306B are overlaid relative to each other such as to be not continuous across surface 410S, with anode connection members 206 reaching across surface 410S but cathode connection members 306B not reaching across the surface. In other embodiments, the reverse can be true and the cathode connection member can reach across while the anode connection member is shorter and does not reach across.

After being stacked as discussed above, at least portions of connection members 206 and 306B are connected to each other. For instance, in one embodiment portions of distal sections 210 and 310B are connected to each other. In one embodiment, distal sections 210 and 310B are edge-welded all along surface 410S. In one embodiment, distal sections 210 and 310B are only connected along portion 410a and 410c of surface 410S. In one embodiment, distal sections 210 and 310B are soldered along surface 410S. In some embodiments, portions of distal sections 310B and 210 are staked, swaged, laser-welded, or connected by an electrically conductive adhesive. In other embodiments, portions of proximal sections 208 are connected to each other and/or portions of proximal sections 308B are connected to each other.

After being connected, portions of connection members 206 and 306B are removed or separated so that proximal sections 208 and 308B are electrically isolated from each other. As used herein, electrically isolated means that sections 208 and 308B are electrically insulated from each other at least up to a surge voltage of the capacitor. For example, dashed lines 451 and 453 define an example of an area that can be removed to electrically isolate the anodes and the cathodes. In various embodiments, different areas can be removed. For example, in one embodiment, a portion of the distal ends 210 of the anodes are removed and the cathode distal sections are not removed at all. In another embodiment, a portion of the commonly positioned section 410c can be removed. Some examples include removing a portion of the distal section 210 of the anode connection member 206 and a portion of the distal section 310B of the cathode connection member 306B. Some examples include removing a portion of the distal section 210 of the anode connection member 206 such that there remains no material or section of the cathode connection member 306B adjacent the anode connection member 206.

Figure 5C:
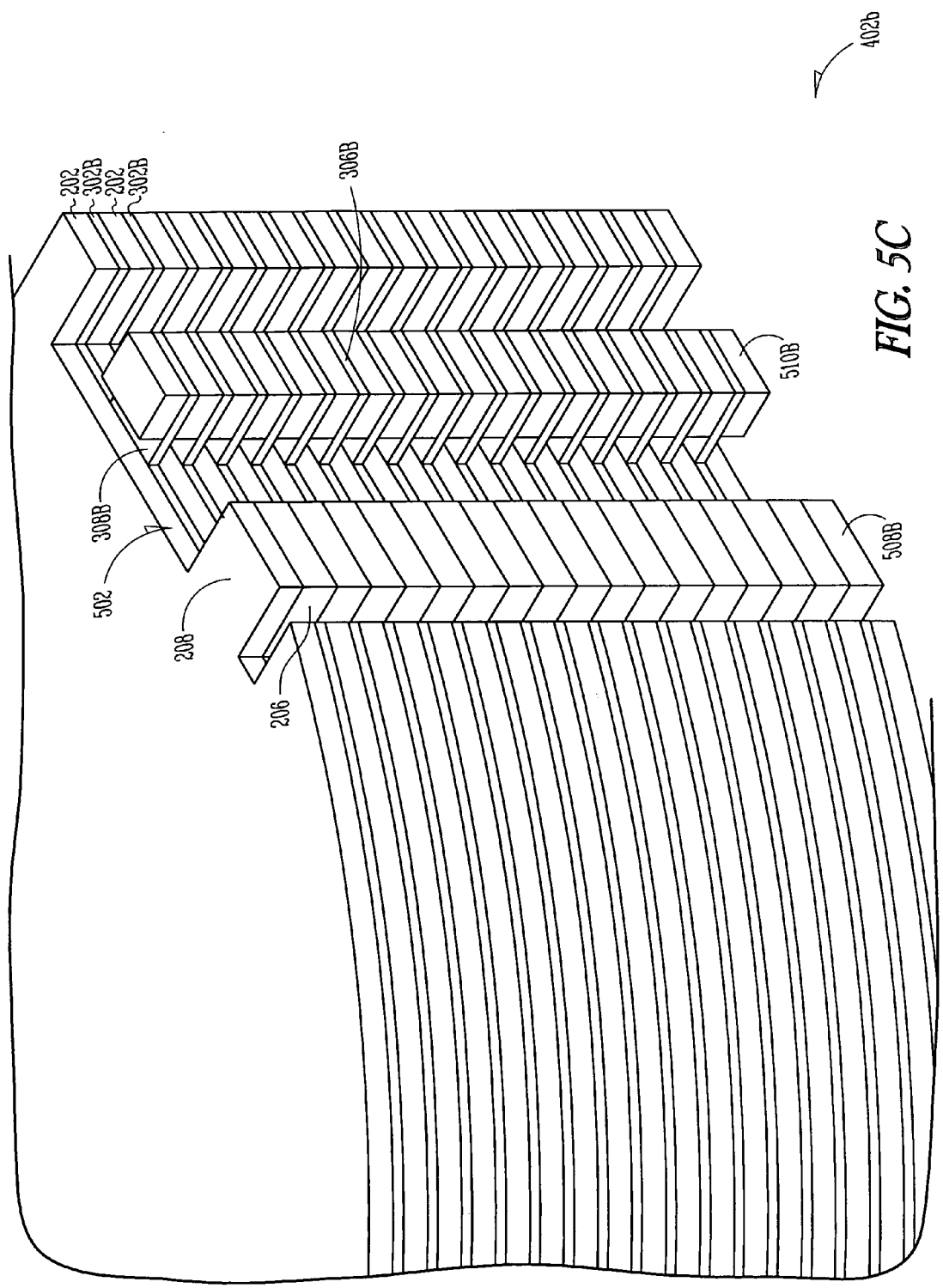
FIG. 5C is a perspective view of the stack of FIG. 5B after the stack has been processed according to one embodiment of the present invention.

FIG. 5C shows stack 402B after portions of distal sections 210 have been removed from the stack, forming a separation 502 between anode connection members 206, which together comprise anode connection section 508B, and cathode connection members 306B, which together comprise cathode connection section 510B. Separation 502 in the present embodiment electrically isolates section 508B from section 510B. Proximal sections 308B are still electrically coupled to each other as are proximal sections 208. In one embodiment, the separation is performed such that cathode connection members 306B include some anode material between each layer, while anode connection members 206 do not include any cathode material between the layers.

In some embodiments, separation 502 is a thin slice. In some embodiments, separation 502 is as wide as cut-outs 214 and 314B, as shown in FIG. 5B. As noted, some examples include removing a portion of the distal section of the anode connection member 206 such that there remains no portion or material of the cathode connection member adjacent the anode connection members 206. This is advantageous since in some examples the cathode layers can include a titanium coating, for example. A titanium coating can interfere with the performance of the anodes or can cause an electrical leakage into the weld or connection between the anodes. The present example keeps all cathode material out of the anode side 508B. In some embodiments, an electrically insulative material is inserted in separation 502. In various embodiments, separation 502 is formed by laser cutting, punching, and/or tool or machine cutting.

Figure 6A:
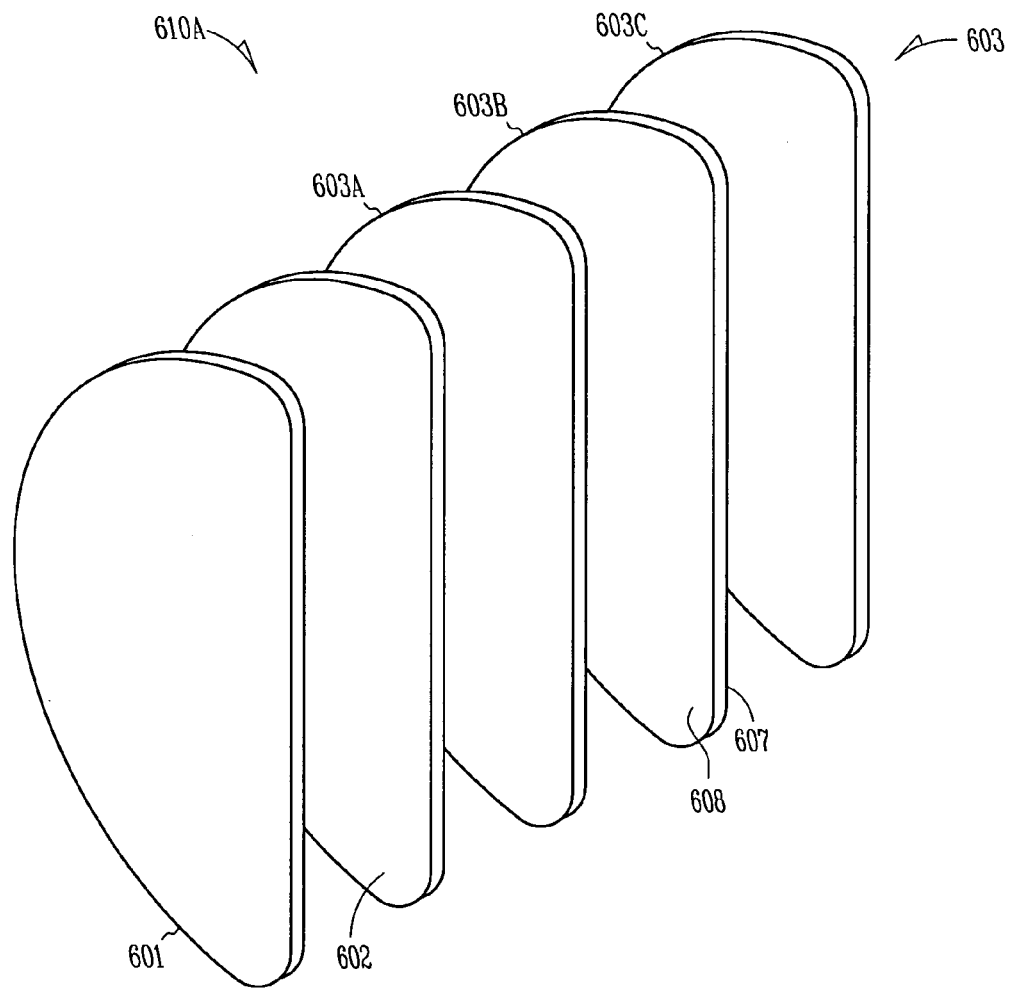
FIG. 6A shows details of one example of a capacitor element 610a, which is representative of capacitor elements 610b–610n, illustrated in the example FIG. 6B, according to one embodiment of the present subject matter.
Figure 6B:
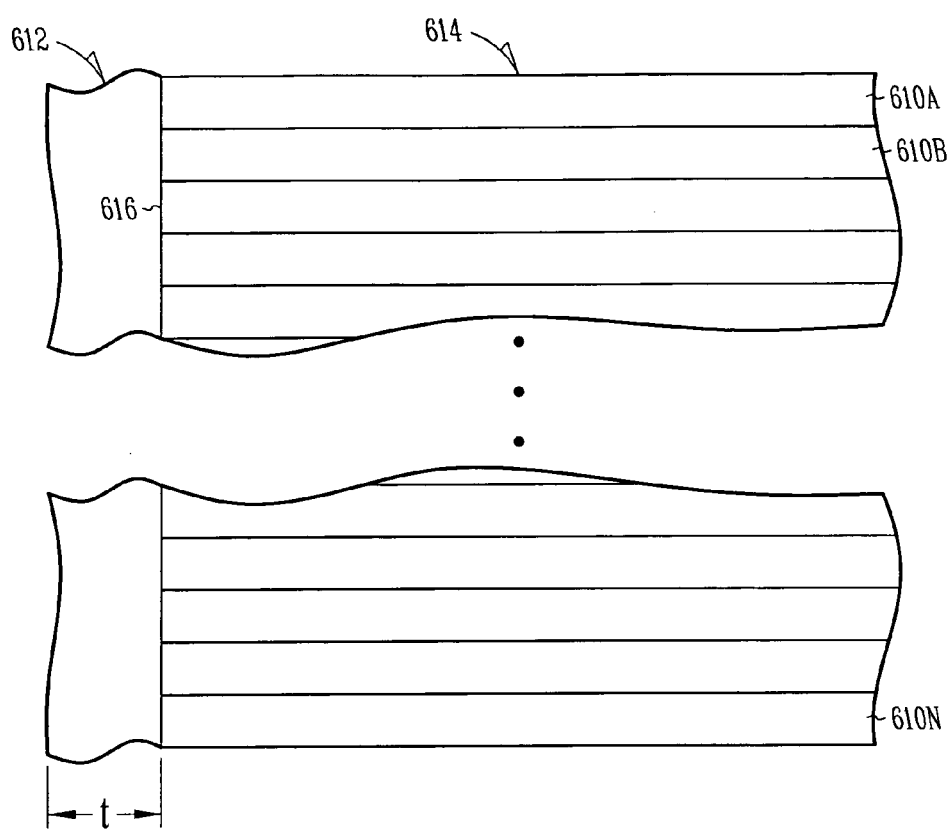
FIG. 6B is a side view of the cross-section "6B" illustrated in FIG. 1, according to one embodiment of the present subject matter.

FIG. 6A shows details of one example of a capacitor element 610a, which is representative of capacitor elements 610b–610n, illustrated in the example FIG. 6B, according to one embodiment of the present subject matter. Element 610a includes a cathode 601, a separator 602, and an anode stack 603. In other embodiments, other numbers and arrangements of anodes, cathodes, and separators are utilized.

Cathode 601 is a foil attached to other cathodes of capacitor stack 614. In some embodiments, cathode 601 can include aluminum, tantalum, hafnium, niobium, titanium, zirconium, and combinations of these metals. In one embodiment, cathode 601 is constructed by taking an aluminum (98% purity or higher) base metal and coating it with titanium oxide, titanium nitride, or titanium pentoxide using sputtering, plating, vacuum deposition, or other coating techniques. In some embodiments, titanium itself is used with a subsequent processing step used to oxidize the titanium resulting in $TiO$, $TiO_2$, $TiN$, $Ti_2O_5$, or other high dielectric constant oxide. Various coatings are present in thicknesses ranging from about 0.5 nanometers to about 6.0 nanometers.

The resulting titanium-coated cathode material has a higher capacitance per unit area than traditional aluminum electrolytic capacitor cathodes. Traditional cathodes which are 98% aluminum purity or higher generally have capacitance per unit area of approximately 250 uF/cm$^2$ for 30 micron thick foil, with an oxide breakdown voltage in the 1–3 volt range. However, a cathode as described above results in a capacitance per unit area which, in some embodiments, is as high as 1000 uF/cm$^2$ or more.

In various embodiments, the present subject matter provides a cathode foil which can be paired with several layers of anodic foil without exceeding the oxide breakdown voltage. When using a traditional cathode to service several layers (2 or more) of anodic foil, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor causing an undesirable mechanical bulge in the layers from the capacitor stack, or in a case. Therefore, in some embodiments, the titanium coated cathode described above serves as a corrective mechanism for hydrogen generation.

Separator 602 is located between each anode stack 603 and cathode 601. In one embodiment, separator 602 consists of two sheets of 0.0005 inches thick kraft paper impregnated with an electrolyte. In some embodiments, separator 602 includes a single sheet or three or more sheets. The electrolyte can be any suitable electrolyte for an electrolytic capacitor, such as an ethylene-glycol base combined with polyphosphates, ammonium pentaborate, and/or an adipic acid solute.

In one embodiment, each anode stack 603 is a multi-anode stack including three anode foils 603a, 603b, and 603c. In other embodiments, anode stack 603 includes one, two, three or more anode foils having a variety of anode shapes. Each anode foil has a major surface 606 and an edge face 607 generally perpendicular to major surface 606. Anodes 603a, 603b, and 603c are generally foil structures and can include aluminum, tantalum, hafnium, niobium, titanium, zirconium, and combinations of these metals.

In one embodiment, anode foils 603a–603c are high formation voltage anode foils, which will be discussed below. In other embodiments, the anode foils are medium and/or low formation voltage foils. In one embodiment, the major surface of each anode foil 603a–603c is roughened or etched to increase its microscopic surface area. This increases the microscopic surface area of the foil with no increase in volume. Other embodiments use tunnel-etched, core-etched, and/or perforated-core-etched foil structures. Other embodiments utilize other foil compositions and classes of foil compositions.

Depending on which process is used to construct the anode, various surfaces are coated with a dielectric. For example, in embodiments where the anode shapes are punched from a larger sheet which has previously been coated with dielectric, only the surfaces which have not been sheared in the punching process are coated with dielectric. In other words, punched shapes include an exposed substrate. But if the dielectric is formed after punching, in various embodiments, all surfaces are coated. In some embodiments, anodes are punched from a larger sheet to minimize handling defects due to handling during the manufacturing process. For example, if a larger sheet is used as a material from which a number of anode layers are punched, machines or operators can grasp the material which is not intended to form the final anode. Generally, in embodiments where the entire anode is not covered with dielectric, the anode must be aged.

FIG. 6B is a side view of the cross-section "6B" illustrated in FIG. 1, according to one embodiment of the present subject matter. In various embodiments, the capacitor stack 614 includes stacked modules or elements 610a, 610b, 610c, . . . , 610n. The example illustration FIG. 6A details the construction of element 610a. In various embodiments, at least two elements are stacked into a capacitor stack 614. The elements include at least a first anode edge face of a first anode and a second anode edge face of a second anode, the first anode edge face and the second anode edge face aligned forming anode connection surface 616. In various embodiments, the anode connection surface 616 is useful for connection of the first anode and the second anode. Various designs can isolate the anode connection surface 616 from a cathode. The examples illustrated in FIGS. 2–5C illustrate various methods and processes for isolating the anode connection surface from the cathode.

It should be noted that while examples demonstrated herein show a planar connection surface, the present subject matter should not be so limited, as any surface is within the scope of the present subject matter. Additionally, examples demonstrated herein show a rectangular stack when viewed from the side, similar to the view in the example FIG. 6B, but additional stack shapes are within the present subject matter. For example, one stack shape within the present subject matter is shaped like a trapezoid when viewed from the side. This embodiment, and other embodiments having other shapes for an anode connection surface 616, including planar and non-planar surfaces, are within the scope of the present subject matter.

In various embodiments, the anode connection surface 616 is covered with a metal having various thicknesses. The metal is applied using various processes, including spraying metal onto the anode connection surface 616. In various embodiments, spraying metal deposits a weld 612 of thickness "t". In various embodiments, the thickness t ranges from about 0.000001 meters to about 0.00005 meters. In additional embodiments, the thickness "t" ranges from about 0.0001 meters to about 0.0002 meters. Metal sprayed onto the anode connection surface 616 both mechanically and electrically links the first anode and the second anode.

In various embodiments, the capacitor stack 614 includes an aligned first element and second element so that a first cathode edge face of a first cathode and a second cathode edge face of a second cathode form a cathode connection surface for electrical connection of the first cathode and the second cathode, and a cathode weld disposed along the cathode connection surface to electrically connect the first cathode and the second cathode.

Figure 7:
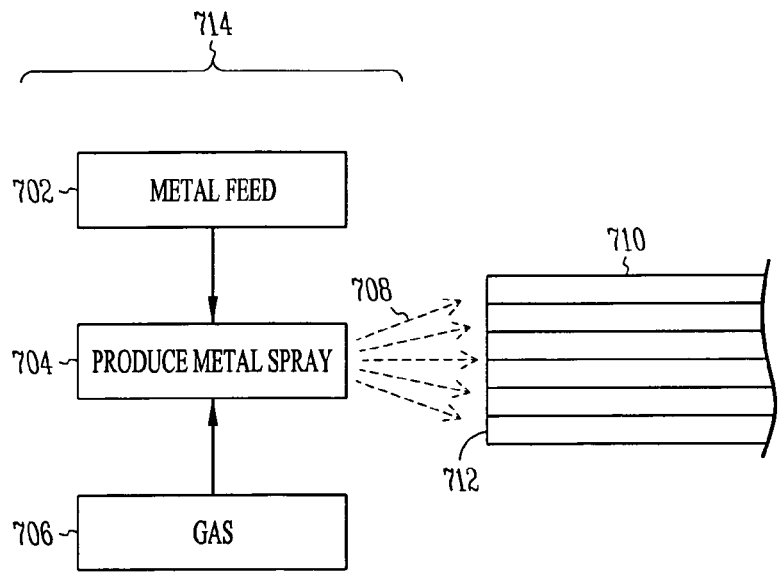
FIG. 7 illustrates a metal spray process, according to one embodiment of the present subject matter.

FIG. 7 illustrates a metal spray process for interconnecting a capacitor stack 710, according to one embodiment of the present subject matter. In various embodiments, the weld is formed by heating aluminum, or an aluminum alloy, to a molten state, and then projecting the molten aluminum onto a capacitor. Heating metal for spraying can be accomplished a number of ways.

Various embodiments heat metal using an oxy-acetylene process. In various embodiments, metal is fed 702 proximal an oxy-acetylene flame 704 while the flame adjusted to melt the metal. Additionally, a pressurized nozzle directs gas 706 toward the melting metal. Directing a gas toward the melting metal at least partially atomizes the metal. Additionally, the atomized metal tends to travel in the direction of the directed gas stream. Thus, a stream of atomized metal may be directed 708 away from the weld head 714.

Additional embodiments use a direct-current arc to heat metal. Embodiments using a direct-current arc induce a voltage between two electrodes in a welding head 714, creating an arc. In various embodiments, the arc is adjusted to melt the metal. Additionally, a pressurized nozzle directs gas 706 toward the melting metal. Directing a gas toward the melting metal at least partially atomizes the metal. Additionally, the atomized metal tends to travel in the direction of the directed gas stream. Thus, a stream of atomized metal may be directed 708 away from the weld head 714.

Additionally, various embodiments heat metal using a pulsed-arc, or spray-arc transfer. A spray-arc transfer induces a voltage between two electrodes in a welding head, creating an arc. Spray-arc welding is characterized by pulsing between low and high current power. Metal is transferred only during the high current pulses. The peak of the high current tends to define a droplet of metal, as the low-current state uses less power than is needed to melt the metal.

In various embodiments, the total average current is lower than with direct current, or nonpulsed-spray arc transfer. Additionally, by controlling the frequency and the amplitude of the pulses, a greater degree of control is realized than over non-pulsed embodiments.

In various embodiments, spraying of metal is controlled so that the metal spray lands on a connection surface 712, such as the anode connection surface, and does not melt the anodes of the anode connection surface. One reason the anodes of the anode connection surface do not melt is that the metal spray has dissipated heat during transmission of the metal spray to the anode connection surface. This can be accomplished by controlling the heat power of the apparatus used to heat the metal, and by controlling the rate of the blowing gas.

Figure 8:
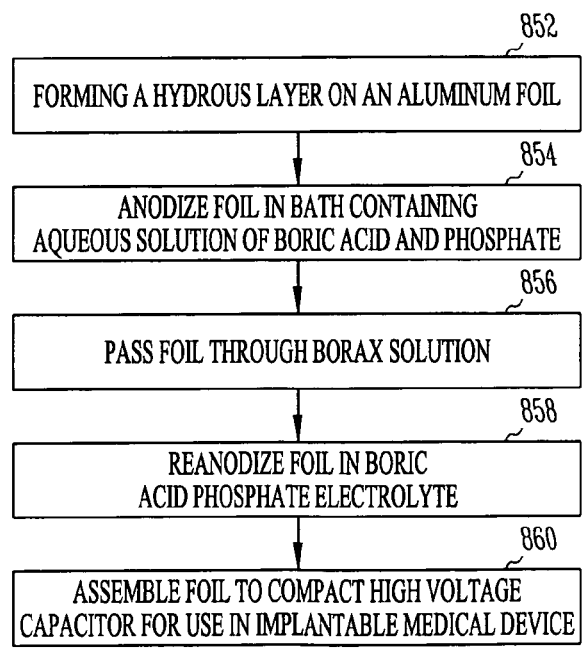
FIG. 8 illustrates an example process for the anodization of aluminum electrolytic capacitor foil, according to the present subject matter.

FIG. 8 illustrates an example process for the anodization of aluminum electrolytic capacitor foil, according to the present subject matter. In varying embodiments, the present subject matter is capable of producing anodized aluminum electrolytic capacitor foil at a formation voltage from about 200 volts to about 760 volts, which can result in a capacitor with a working voltage from about 150 volts to about 570 volts. For example, the present subject matter encompasses aluminum oxide formed at between approximately 600 volts and approximately 760 volts. Additionally, the present subject matter encompasses embodiments where anodization occurs from about 653 volts to about 720 volts. Additionally, the present subject matter encompasses embodiments wherein anodization occurs from about 667 volts to about 707 volts during formation.

Additionally, the present subject matter is capable of producing an aluminum electrolytic capacitor foil which can deliver about 5.3 joules per cubic centimeter of capacitor stack volume to about 6.3 joules per cubic centimeter of capacitor stack volume, at a voltage of between about 150 volts to about 570 volts.

Varied processes can be utilized to produce the aluminum foil of the present subject matter. For example, one process includes forming a hydrous oxide layer on an aluminum foil by immersing the foil in boiling deionized water 852. The aluminum foil is also subjected to electrochemical anodization in a bath containing an anodizing electrolyte 854 composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution 856. Borax, in various embodiments, includes a hydrated sodium borate, $Na_2B_4O_7.10H_2O$, and is an ore of boron.

In varying embodiments, the foil is reanodized in the boric acid-phosphate electrolyte previously discussed 858. In various embodiments of the present subject matter, the process produces a stabilized foil suitable for oxide formation of up to approximately 760 volts.

In various embodiments, the anodizing electrolyte used in block 854 and 856 contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes a an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a the barrier layer oxide of lower quality, and foil corrosion.

Various aspects of the present subject matter include performance properties which enable the capacitor to function as a single capacitor in an implantable cardioverter defibrillator 860. For example, by constructing the capacitor stack with the methods and apparatus contained in these teachings, one may construct a capacitor which is suited for use as the sole capacitor used for powering therapeutic pulses in an implantable cardioverter defibrillator. By using a single capacitor, instead of two capacitors which are connected in series, the present subject matter contributes to weight and size reductions.

Overall, the present subject matter offers multiple advantages. First, the present subject matter features capacitor designs which are compact and lightweight due to improved interconnections. Smaller capacitors can be used in electric devices of reduced size. Next, the present subject matter enables multiple options for making interconnections, enabling multiple capacitor shapes. By spraying an interconnect, the interconnect can adapt to a wider range of connection surface shapes. Also, the present subject matter benefits capacitor design by providing a high-speed method for interconnection of capacitor parts. High-speed methods are adapted for high-volume production, which can lower capacitor cost.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments, will be apparent to those of skill in the art upon reviewing the above description. The scope of the present subject matter should be determined with reference to the appended claims, along with the full scope of equivalents to which such claims are entitled.

I claim:

1. A capacitor stack, including a first element having at least one first anode and at least one first cathode and a second element having at least one second anode and at least one second cathode, the capacitor stack formed by the process comprising:

aligning the first element and the second element so that a first anode edge face of the first anode and a second anode edge face of the second anode form an anode connection surface for electrical connection of the first anode and the second anode; and spraying metal on the anode connection surface to electrically connect the first anode and the second anode.

2. The capacitor stack of claim 1, additionally comprising:
aligning the first element and second element so that a first cathode edge face of the first cathode and a second cathode edge face of the second cathode form a cathode connection surface for electrical connection of the first cathode and the second cathode; and
spraying metal on the cathode connection surface to electrically connect the first cathode and the second cathode.

3. The capacitor stack of claim 1, wherein spraying metal includes atomizing the metal with an oxy-acetylene heat source, and blowing the metal toward the anode connection surface.

4. The capacitor stack of claim 1, wherein spraying metal includes atomizing the metal with an pulsed-arc heat source, and blowing the metal toward the anode connection surface.

5. The capacitor stack of claim 1, wherein spraying metal includes atomizing the metal with a direct current arc heat source, and blowing the heated metal toward the anode connection surface.

6. The capacitor stack of claim 3, 4, or 5, wherein spraying metal includes depositing a weld onto the anode connection surface, the weld having heat insufficient to melt the anode connection surface.

7. The capacitor stack of claim 1, wherein each element includes at least one cathode, at least one anode, and a separator disposed between the at least one anode and the at least one cathode.

8. The capacitor stack of claim 7, wherein each element is aligned with an anode connection member extending away from the element and a cathode connection member extending away from the element.

9. The capacitor stack of claim 8, wherein the first element and the second element are in alignment, a first anode connection member of the first element in alignment with a second anode connection member of the second element.

10. The capacitor stack of claim 1, wherein spraying metal deposits a weld, the weld having a thickness from about 0.000001 meters to about 0.0005 meters.

11. The capacitor stack of claim 10, wherein spraying metal deposits a weld, the weld having a thickness from about 0.0001 meters to about 0.0002 meters.

12. The capacitor stack of claim 1, wherein the capacitor stack is adapted to deliver from about 5.3 joules per cubic centimeter of capacitor stack volume to about 6.3 joules per cubic centimeter of capacitor stack volume, at a voltage of approximately 465 volts to approximately 620 volts.

13. The capacitor stack of claim 1, wherein the capacitor stack includes from about 16 cathodes to about 22 cathodes, and from about 52 anodes to about 64 anode.

14. The capacitor stack of claim 13, wherein the capacitor stack includes approximately 20 cathodes, and approximately 58 anodes.

15. A method, comprising:
forming a first element by stacking a first anode and a first cathode, the first element having a first anode edge face;
forming a second element by stacking the second anode and the second cathode, the second element having a second anode edge face for electrical connection to the first anode edge face;
stacking the first element and the second element;
aligning the first anode edge face with the second anode edge face, the alignment defining an anode connection surface; and
spraying metal onto the anode connection surface to form a weld, the weld connecting the first anode and the second anode and forming a capacitor stack.

16. The method of claim 15, additionally comprising:
connecting an anode conductor to the capacitor stack;
disposing the capacitor stack in a case with a first aperture and a second aperture, the anode conductor stack sealingly extending through the second aperture and conforming to the material defining the second aperture; and
sealingly connecting a lid to the first aperture, the lid conforming to the material defining the first aperture.

17. The method of claim 16, wherein the capacitor is disposed in an implantable medical device including programmable pulse generation electronics.

18. The method of claim 15, wherein the first anode and the second anode include a metallic substrate partially covered with the oxide, wherein the first anode edge face of the first anode includes a first exposed substrate, and the second anode edge face of the second anode include a second exposed substrate; and wherein spraying metal includes depositing metal on the first exposed substrate and the second exposed substrate.

19. The method of claim 15, additionally comprising aging the capacitor stack and a weld, the weld formed by spraying metal onto the anode connection surface.

20. The method of claim 15, additionally comprising:
aligning the first element and second element so that a first cathode edge face of the first cathode and a second cathode edge face of the second cathode form a cathode connection surface for electrical connection of the first cathode and the second cathode; and
spraying metal on the cathode connection surface to electrically connect the first cathode and the second cathode.

21. The method of claim 15, wherein spraying metal includes atomizing the metal with an oxy-acetylene heat source, and blowing the metal toward the anode connection surface.

22. The method of claim 15, wherein spraying metal includes atomizing the metal with a pulsed-arc heat source, and blowing the metal toward the anode connection surface.

23. The method of claim 15, wherein spraying metal includes atomizing the metal with a direct current arc heat source, and blowing the heated metal toward the anode connection surface.

24. The method of claim 21, 22, or 23, wherein spraying metal includes depositing a weld onto the anode connection surface, the weld having heat insufficient to melt the anode connection surface.

25. The method of claim 15, wherein etching a first sheet includes applying an etchant resistant mask to the first anode and the second anode, the etchant resistant mask defining a first connection member and a second connection member, etching the first anode and the second anode, and removing the etchant resistant mask from the first anode and the second anode; and wherein aligning the first anode edge face with the second anode edge face includes aligning the first connection member and the second connection member such that the first connection member and the second connection member form the anode connection surface.

26. The method of claim 15, wherein spraying metal deposits a weld, the weld having a thickness from about 0.000001 meters to about 0.0005 meters.

27. The method of claim 25, wherein spraying metal deposits a weld, the weld having a thickness from about 0.0001 meters to about 0.0002 meters.

* * * * *